US006748046B2

(12) United States Patent
Thayer

(10) Patent No.: US 6,748,046 B2
(45) Date of Patent: Jun. 8, 2004

(54) OFF-CENTER TOMOSYNTHESIS

(75) Inventor: Dale Thayer, San Diego, CA (US)

(73) Assignee: Teradyne, Inc., Boston, MA (US)

( * ) Notice: Subject to any disclaimer, the term of this patent is extended or adjusted under 35 U.S.C. 154(b) by 0 days.

(21) Appl. No.: 09/731,335

(22) Filed: Dec. 6, 2000

(65) Prior Publication Data

US 2003/0058983 A1 Mar. 27, 2003

(51) Int. Cl.$^7$ .............................................. G01N 23/04
(52) U.S. Cl. ............................. 378/22; 378/2; 378/21
(58) Field of Search .......................... 378/22, 2, 21, 378/25, 10, 207

(56) References Cited

U.S. PATENT DOCUMENTS

| | | | | |
|---|---|---|---|---|
| 4,688,241 A | * | 8/1987 | Peugeot | 378/137 |
| 4,926,452 A | * | 5/1990 | Baker et al. | 378/22 |
| 5,259,012 A | * | 11/1993 | Baker et al. | 378/21 |
| 5,583,904 A | * | 12/1996 | Adams | 378/22 |
| 5,594,770 A | * | 1/1997 | Bowles et al. | 378/58 |
| 5,668,844 A | * | 9/1997 | Webber | 378/2 |
| 5,687,209 A | * | 11/1997 | Adams | 378/22 |
| 5,710,063 A | * | 1/1998 | Forehand et al. | 437/208 |
| 5,719,952 A | * | 2/1998 | Rooks | 382/150 |
| 5,760,403 A | * | 6/1998 | Elabd | 250/370.11 |
| 5,872,828 A | * | 2/1999 | Niklason et al. | 378/23 |
| 6,028,910 A | * | 2/2000 | Kirchner et al. | 378/22 |
| 6,222,902 B1 | * | 4/2001 | Lin et al. | 378/22 |
| 6,324,249 B1 | * | 11/2001 | Fazzio | 378/22 |

OTHER PUBLICATIONS

International Search Report.

* cited by examiner

Primary Examiner—David V. Bruce
Assistant Examiner—Irakli Kiknadze
(74) Attorney, Agent, or Firm—Matthew J. Sampson; McDonnell Boehnen Hulbert & Berghoff

(57) ABSTRACT

The present invention is directed to an apparatus and method for acquiring off-axis X-ray images of a plurality of regions of interest. The apparatus includes a source producing a beam of radiation, a surface to support at least a subset of the plurality of regions of interest, and a X-ray detector located to simultaneously receive portions of the beam that have passed through the subset of the plurality of regions of interest. The X-ray detector produces from the received portions of the beam an electronic representation of an image for each region of interest in the subset of the plurality of regions of interest. Any combination of the source, the surface, and the detector may be moveable to position the regions of interest within the beam.

34 Claims, 7 Drawing Sheets

OFF-CENTER TOMOSYNTHESIS

FIELD OF THE INVENTION

The present invention relates generally to imaging inspection systems and methods. Specifically, the present invention relates to an X-ray inspection system using tomosynthesis imaging techniques.

BACKGROUND OF THE INVENTION

The mounting of Integrated Circuits ("IC") chips on Printed Circuit Boards ("PCBs") requires inspection of the interconnections on the PCBs to determine whether the interconnections contain significant defects. Continual increases in the IC chip complexity, performance, and placement density place demands on the density and functionality of package interconnections. The Ball-Grid-Array ("BGA") is one example of a Surface-Mount-Technology ("SMT") package with interconnections that demand specialized inspection techniques. The continually increasing complexity and density of the PCB interconnections have resulted in the development of a number of interconnection inspection techniques for detecting defects on or within the interconnections.

One such interconnection inspection technique, tomosynthesis, is capable of detecting defects by creating a digital image representation of a sliced view along a single plane passing through a three-dimensional electrical solder joint connection. A digital tomosynthesis system makes it possible to inspect various PCB solder joint qualities, which cannot be inspected by visual methods or conventional X-ray radiography methods. U.S. Pat. No. 4,688,241 issued on Aug. 18, 1987 to Richard S. Peugeot, incorporated herein by reference, discloses a number of tomosynthesis inspection systems, including a system 10 depicted in FIG. 1 of the instant application. The system 10 includes a steerable microfocus X-ray source 12, a large-format image detector 30 capable of imaging X-rays, and an inspection plane 20 positioned between the source and the detector. As used herein, the term "steerable" in reference to the source 12 refers to the capability to direct an electron beam within the source 12 to various locations on a target anode. In contrast, a stationary or non-steerable source, as used herein, refers to a source that lacks such capability, i.e. the electron beam strikes the target anode at a single location.

The regions A, B, and C to be imaged may be placed on an X-Y table (not shown), which lies in the inspection plane 20. When an object is on the X-Y table, the test object may be translationally moved along the x and y directions so that a region of interest, such as a solder joint, can be imaged. The source 12 produces an X-ray beam 50 having sufficient energy to penetrate the test object and reach the detector 30, while also having a low enough energy so that a resulting image has contrast within the region of interest.

The X-ray source 12 and the detector 30 may be mounted on independent vertical drive mechanisms allowing a continuously variable field-of-view, ranging from approximately 2.5 mm×2.5 mm to approximately 25 mm×25 mm, to be obtained. In particular, the X-ray source 12 is mounted on a programmable Z-axis, which changes the distance between the X-ray source 12 and the inspection plane 20. The distance between the X-ray source 12 and the plane 20 is referred to herein as Z1. The detector is also mounted on a programmable Z-axis, which changes the distance between the inspection plane 20 and the detector 30. The distance between the inspection plane 20 and the detector 30 is referred to herein as Z2. Variation of the field of view may be accomplished by varying either or both distances Z1 and Z2.

The operation of the system of FIG. 1 now will be explained. A circuit board having regions of interest A, B, and C is positioned on the X-Y table, in the inspection plane 20. The board is then moved translationally along the x and y directions so that a region of interest A, B, or C, such as a solder joint, or a component can be imaged. Once the board is properly positioned, a beam of radiation, such as X-ray beam 50, is projected towards an object on the circuit board. A portion of the X-ray beam 50 transmits through and is modulated by the object.

The portion of the beam 50 that passes through the object then strikes the image detector 30. The detector 30 is capable of producing an X-ray shadowgraph containing the modulation information from the test object. The X-rays striking the input screen of the detector 30 produce a visible light or shadowgraph image of the volume of the object that falls within the X-ray beam 50. If the detector 30 includes an image intensifier, the image at the output of the image intensifier is amplified in brightness.

The image that appears on the output face of the detector 30 is viewed, through a mirror, by a video camera (not shown). The images from various regions of the detector 30, such as the regions numbered 1, 3, 5 and 7 in FIG. 1, may be sequentially directed to the camera by adjusting the position of the mirror.

The resulting images are then input into a video digitizer. The video digitizer provides as an output digitized image sets. Each image in the set is supplied to a memory and stored. The images may then be separately fed into a tomosynthesis computer, which is programmed with a known tomosynthesis algorithm that effects a combination of the images and provides a resultant image to a monitor. In order to improve the resolution of the digitized image sets, it is desirable to limit the field of view of the camera to a region of the detector 30, such as the regions 1, 3, 5 or 7, rather than to acquire images for tomosynthesis viewing the entire detector 30.

For system 10, the center of the region of interest must coincide with a line extending from the center of the path of the x-ray source to the center of the detector 30. As can be seen in FIG. 1, the center of object B coincides with the centerline of X-ray beam 50 and the center of the field of view of detector 30.

To acquire tomosynthetic images for object B, for example, the X-ray source 12 is positioned at multiple points 1-8 along a circular path that is perpendicular to the Z axis. Each point on the circle falls in a plane that is perpendicular to the Z axis and maintains the same angle with, or is equidistant from, the Z axis. At each point, the X-ray source 12 emits an X-ray beam 50 towards, and at least partially through, the object B, thereby generating an image of object B at the detector 30. For example, to acquire image 1 for object B, the X-ray source 12 is steered to position 1 and the detector field of view is moved to position 1. This process is repeated for images 2 through 8 of object B. The 8 images are acquired sequentially since the electron beam inside the X-ray source housing and the detector field of view must be moved after each acquisition. As a result, 8 scanned images of object B at a known pre-determined angle are captured.

After the required images of object B are taken, then the X-Y table is moved so that the center of object A coincides with the centerline of the X-ray beam 50 and the center of the detector field of view. To acquire image 1 for object A, the X-ray source 12 is steered to position 1 and the detector field of view is moved to position 1. This process is repeated for images 2 through 8 of object A. Thus, 8 scanned images of object A are captured. This process is continued for each of the objects, or regions of interest, to be imaged.

In order for tomosynthesis to be effective, the angle phi should be at least a 25–30 degree angle from perpendicular to generate a useful tomosynthetic slice of the object. However, the practical limitations of the diameter of the X-ray source, the diameter of the detector, the distance between the source and the object, Z1, and the distance between the object and the detector, Z2, result in compromises to be made with respect to the angle that can be achieved, the field-of-view, the resolution, and the speed of the system. In order to achieve the desired angle and thus a useful tomosynthetic slice, a costly X-ray source and/or detector are required.

As mentioned above, conventional tomosynthesis techniques, such as those shown by Peugeot in U.S. Pat. No. 4,688,241 and depicted in FIG. 1, require that the centerline of the X-ray focal spot position and of the field of view at the detector is coincident with the center of the object to be imaged. There are a number of resultant advantages from this arrangement. Passing the X-ray beam through the center of the region of interest simplifies calibration of the machine, the dewarping and gray correction of the images, and the mechanical positioning of the object. The quality of the tomosynthetic slice depends on accurate positioning of the electron beam and mirrors. This accuracy can be achieved with existing technology for electromagnetic beam steering and galvonometer mirrors. A disadvantage of conventional systems, however, is that they require the use of a large-format detector and a steerable X-ray source. Such equipment is expensive and its use increases the overall cost of the system. Further, with such systems, it is slower to sequentially acquire each one of the 8 images, thus limiting the speed of the system to 8 times the time it takes to acquire one image.

Thus, there is a need for an X-ray inspection system using a tomosynthesis imaging technique that does not require the centerline of the X-ray focal spot position and of the field of view at the detector to be coincident with the center of the object to be imaged.

There is a further need in the art for an X-ray inspection system using a tomosynthetic imaging technique that does not require both a steerable X-ray source and a large-format detector.

There is yet a further need in the art for an X-ray inspection system using a tomosynthesis imaging technique that increases the throughput of the system while decreasing its overall cost.

SUMMARY OF THE INVENTION

The present invention meets the needs of the prior art by providing an X-ray inspection system using a tomosynthesis imaging technique that does not require the centerline of the X-ray focal spot position and the field of view at the detector to be coincident with the center of the object to be imaged. With this requirement eliminated, significant cost and performance advantages are realized by avoiding the use of either a large-format detector or a steerable X-ray source or both.

These advantages can be achieved by using an inspection system having a non-steerable X-ray source combined with an X-ray detector that can capture 8 images simultaneously. Thus, the need for a costly steerable X-ray source is eliminated and the overall system is simplified. Further, the speed or throughput of the system is improved.

These advantages can be alternatively realized by using an inspection system having a steerable X-ray source and a small-format high-resolution detector. By steering the X-ray source further off-center, the image of the object can be projected onto a high resolution, small-format detector. Thus, cost savings are achieved by using a smaller, less expensive detector.

Since X-ray detectors and steerable X-ray sources are typically the most expensive components in the inspection system, decreasing the cost of one or both would decrease overall system cost while still maintaining the required performance.

The present invention also reduces the number of mechanical repositioning movements required to place the X-ray source or the detector and the target object in position for tomography. Therefore, the present invention enables images of complex interconnections to be created in less time with less expense.

DETAILED DESCRIPTION OF THE PRESENTLY PREFERRED EMBODIMENTS

The presently preferred embodiments are described herein with reference to FIGS. 2 through 6. Though the choice of objects, or regions of interest, to be imaged is arbitrary, the objects to be imaged preferably comprise either an electronic assembly or a circuit board including electronic components connected to a circuit board through solder joints.

Figure 1:
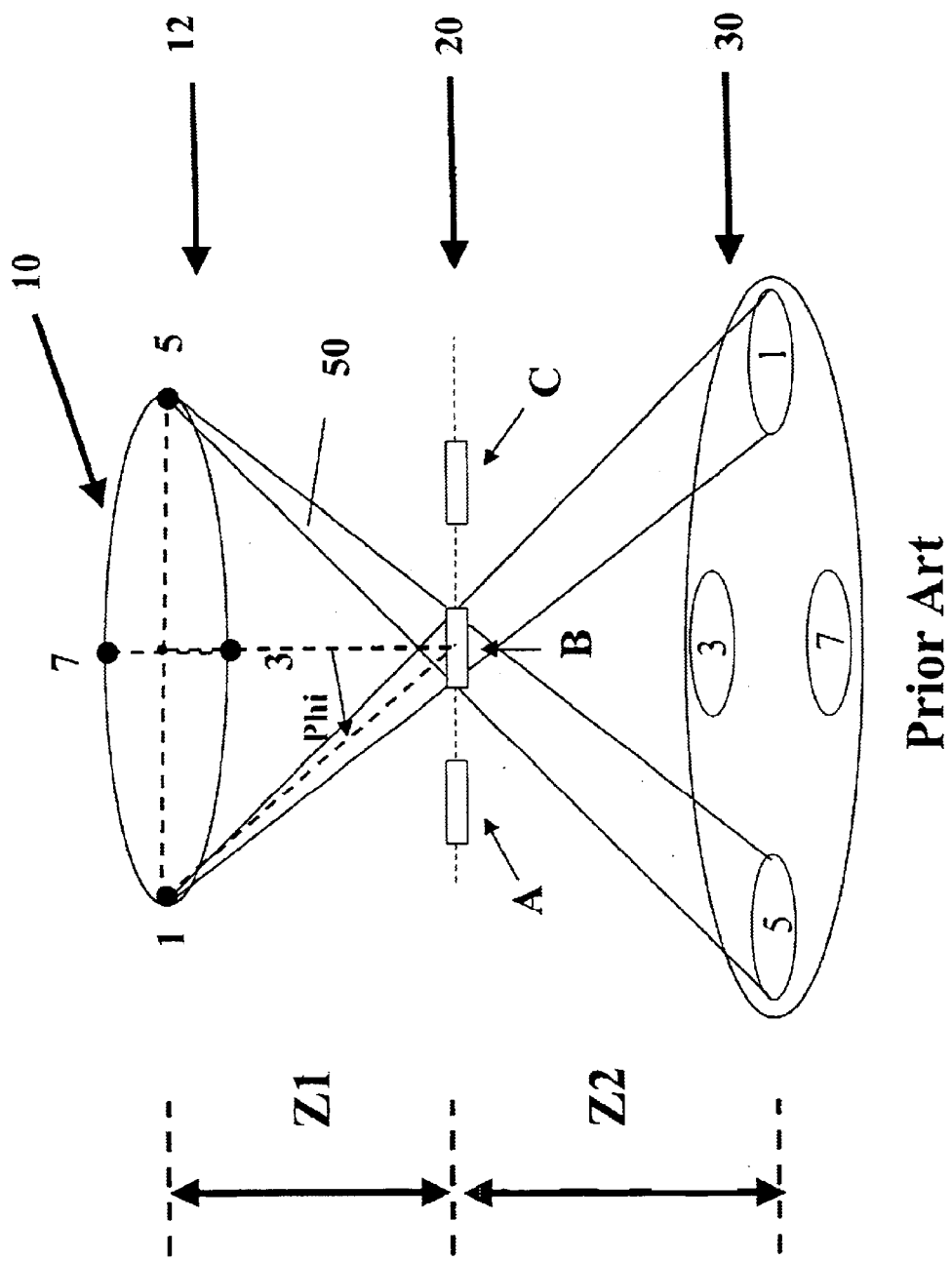
FIG. 1 is a diagrammatic illustration of an X-ray inspection system of the prior art.
Figure 2:
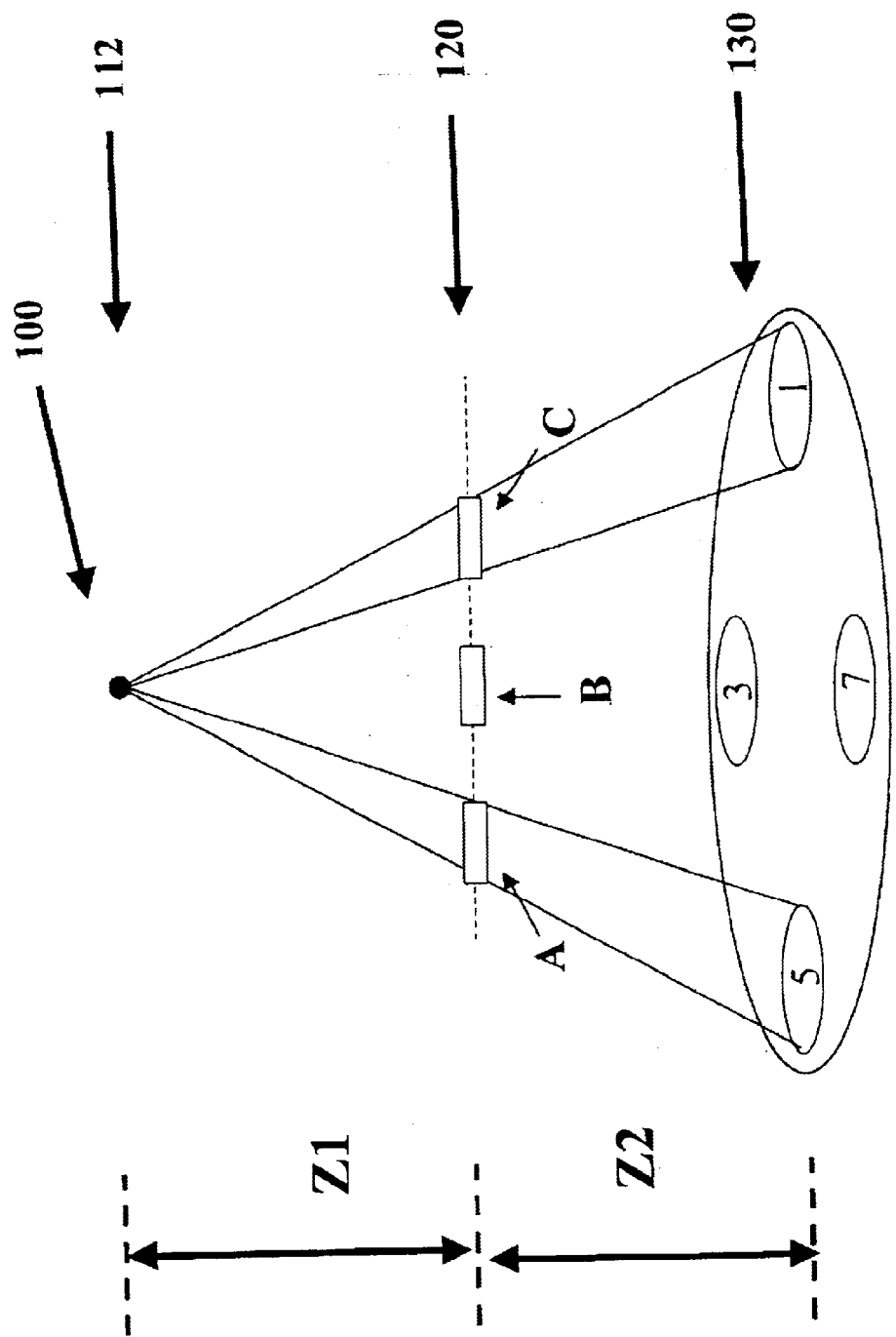
FIG. 2 is a diagrammatic illustration of one embodiment of an X-ray inspection system of the present invention.
Figure 2A:
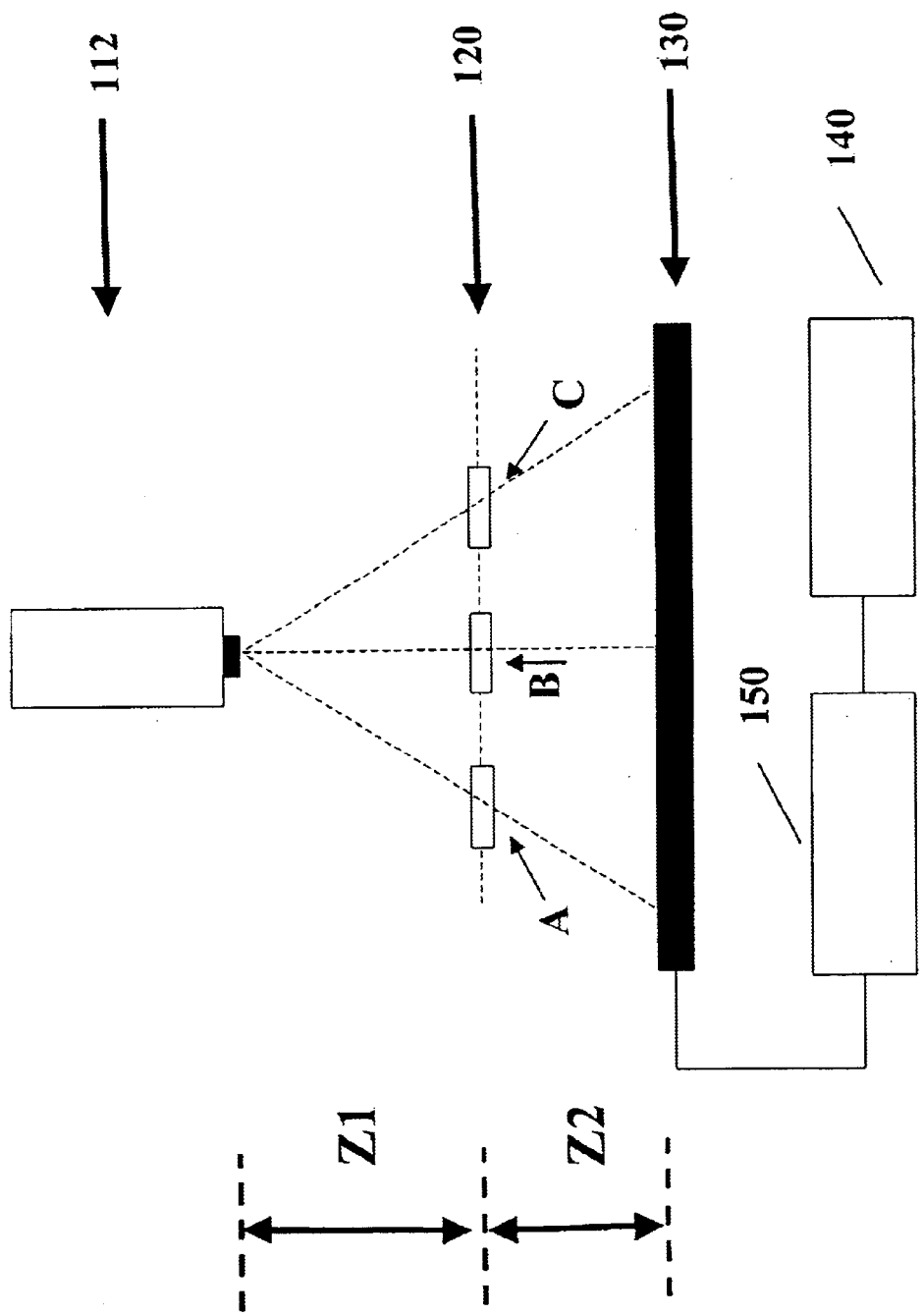
FIG. 2a is a further diagrammatic illustration of the embodiment of FIG. 2.

FIGS. 2 and 2a each depict an X-ray inspection system 100 embodying the principles of a first embodiment of the present invention. The system 100 includes a non-steerable X-ray source 112 and an area detector 130. A suitable non-steerable X-ray source is available from Nicolet Imaging Systems, San Diego, Calif. The source 112 is displaced from and generally centered with respect to the center of an inspection plane 120 and the center of the detector 130. As with the system of FIG. 1, the regions A, B, and C to be imaged are mechanically supported in the inspection plane 120. The support surface may be capable of moving the regions A, B, and C relative to the source 112 and the detector 130, such as where the support is an X-Y table. Alternatively, the support surface may simply hold the regions at a predetermined location relative to the source 112 and/or the detector 130. Although A, B, and C may be referred to herein as objects, those skilled in the art will appreciate that A, B, and C may simply be different regions of interest within the same physical object.

The X-ray source 112 and the detector 130 are preferably mounted on independent vertical drive mechanisms that allow a continuously variable field-of-view. The vertical drive mechanisms are used to vary the distance, Z 1, between the X-ray source 112 and the object to be imaged, and the distance, Z2, between the object to be imaged and the detector 130. In system 100, the distance Z1 can range from approximately 0.5" to 3.0" and the distance Z2 can range from approximately 0.5" to 3.0". Alternatively, the mechanical support for the regions A, B, and C, and at least one of the source 112 and the detector 130 may be mounted on independent vertical drive mechanisms to allow Z1 and Z2 to vary independently. As a further alternative, the system may not include vertical drive mechanisms, the source 112 and the detector 130 may be positioned at fixed Z1 and Z2 distances. In addition, although FIG. 2 illustrates that the source 112 is located above the inspection plane 120 and the detector 130 below it, those skilled in the art will recognize that the source 112 may alternatively be disposed below, and the detector 130 above, the inspection plane 120.

System 100 may be provided with an X-ray detector 130 having a flat screen and at least 1000 pixels in each direction. In accordance with a preferred embodiment, the detector 130 is an amorphous silicon ("aSi") detector. An aSi detector comprises a flat screen made of aSi with a coating of Cesium Iodide ("CsI") crystals. An example of such an aSi detector is the Model FlashScan 20, available from Trixell, Moirans, France. This particular model has 1536 pixels in one direction and 1920 pixels in the other, and a resolution of 4 linepairs/mm. It has a 127 micron pixel size and hence a total detector size of approximately 195 mm×244 mm.

When X-rays hit the screen of the aSi detector, the X-rays are absorbed in a layer of CsI. Since CsI is a scintillating material, it subsequently emits pulses of light. This light is then converted within the detector 130 into electrical charge carriers in a matrix of aSi photodiodes. Every photodiode is connected to read-out circuitry by an individual switch, which may be a thin film transistor or a diode. The output signals are amplified and converted from analog to digital. Via fiber optic or other electrically conductive links, the image data can be transferred to a real time image processing system, which processes the image formation to formulate an image. The resulting images may then be viewed on a display or video monitor 140, shown in FIG. 2a, or stored for later retrieval.

With conventional tomosynthesis, the output of the detector is supplied to a camera by a mirror, which in turn is fed into a video processor. Because the output of the detector 130 described above is itself a digital representation of the x-ray image, the need for a mirror and a camera is eliminated, and the output of the detector is provided directly to an image processing system. Notably, since the aSi detector 130 is large enough to achieve a 30 degree angle for off-axis images with at least 512 pixels in each image, all eight images can be acquired simultaneously, as further described below, thereby decreasing the time required for inspection dramatically.

Additionally, system 100 is provided with a control system. The control system functions to locate the object to be imaged at the desired position within the inspection plane 120, whether by moving the object, the source, the detector or some combination of the foregoing. The system also controls the operation of the independent vertical drive mechanisms, if utilized, to vary the distances Z1 and Z2, as required, and the image stitching aspect of the present invention, discussed in detail below.

The functions of the control system may be performed by a processor 150, shown in FIG. 2a, which may also perform the real time image processing functions described above. Thus, the processor 150 may be a general purpose microprocessor that is programmed, as known to those skilled in the art, to perform the control system and image processing functions. Alternatively, the processor 150 may be a dedicated image processing device, in which case the control functions may be performed by a separate microprocessor based device or a separate controller.

Referring back to FIG. 2, when the source 112 projects an X-ray beam toward regions in the inspection plane 120, an off-axis image of region A will be obtained at position 5 on the detector 130, as well as an off-axis image of object C corresponding to position 1. Off-axis images of other regions not shown in FIG. 2 could also be obtained. This will be better understood with the following discussion. For simplicity's sake, the discussion is limited to four images, although more images may be required for tomosynthetic reconstruction. For typical solder connection inspections, it has been found that eight off-axis images will usually provide acceptable results, although more or fewer images may alternatively be used.

Figure 4:
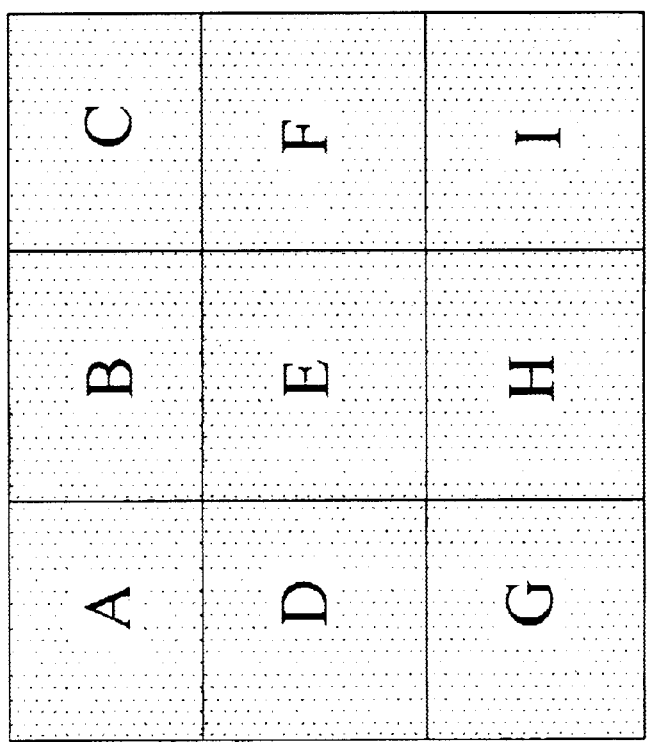
FIG. 4 is an illustration of the regions to be imaged on a printed circuit board.

FIG. 4 depicts nine possible areas of interest to be imaged on a printed circuit board. When area of interest A is placed in the center of the inspection plane 120 and X-rays are projected from the non-steerable source 112, an off-axis image of area B, corresponding to detector position 1, will be obtained, as well as an off-axis image of area D, corresponding to detector position 7. When area of interest B is placed in the center of the inspection plane 120 and X-rays are projected from non-steerable source 112, an off-axis image of area A, corresponding to detector position 5, will be obtained as well as an off-axis image of area E, corresponding to detector position 7 and an off-axis image of area C, corresponding to detector position 1. When area of interest C is placed in the center of the inspection plane 120, an off-axis image of area B, corresponding to detector position 5, will be obtained as well as an off-axis image of area F, corresponding to detector position 7. When area of interest D is placed in the center of the inspection plane 120, an off-axis image of area A, corresponding to detector position 3, will be obtained as well as an off-axis image of area E, corresponding to detector position 1 and an off-axis image of area G corresponding to detector position 7. When area of interest E is placed in the center of the inspection plane 120, an off-axis image of area D, corresponding to detector position 5, will be obtained as well as an off-axis image of area F corresponding to detector position 1, an off-axis image of area B, corresponding to detector position 3, and an off-axis image of area H, corresponding to detector position 7. The remaining areas of interest are placed in position and the corresponding images are obtained.

Figure 5:
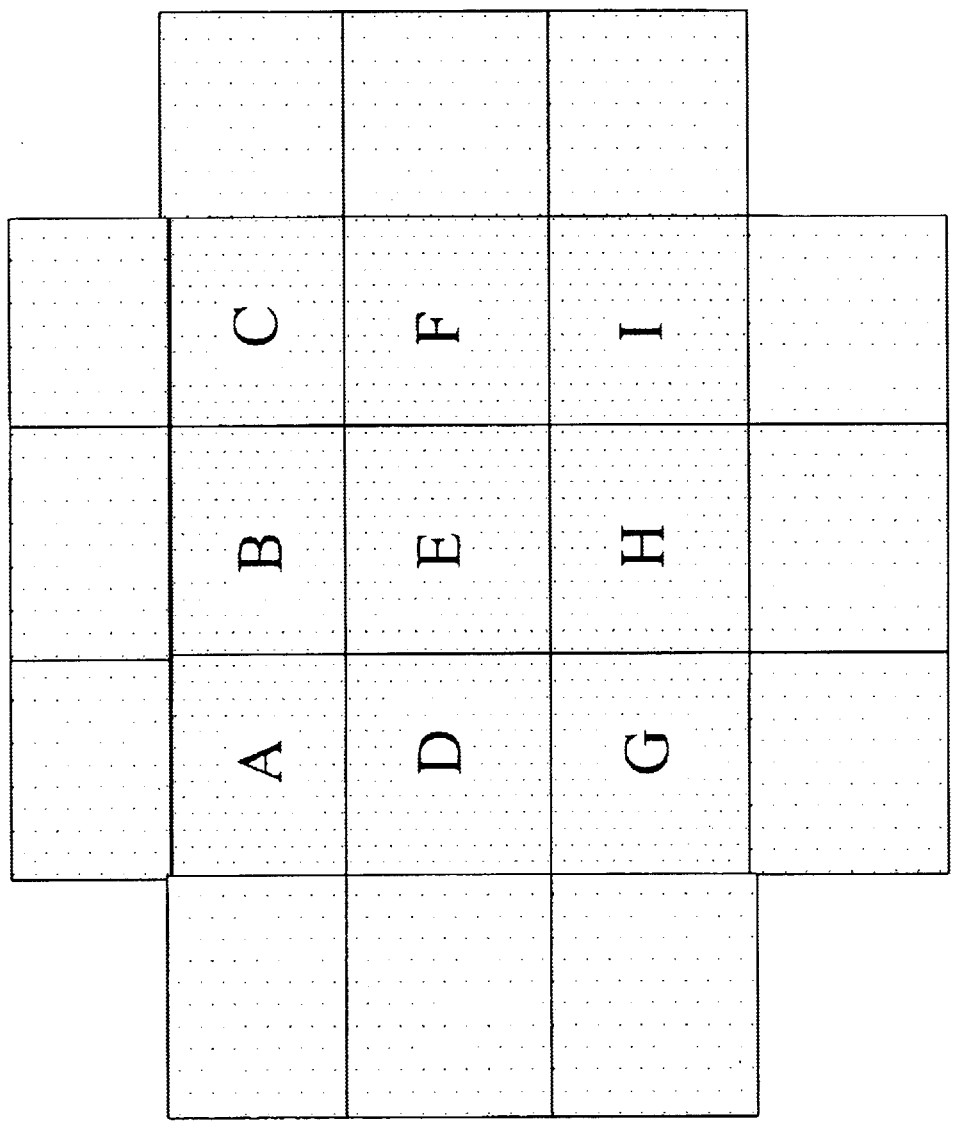
FIG. 5 is similar to FIG. 4 and further illustrates the additional locations to which the centerline of the X-ray beam must be located in order to acquire all the necessary off-axis images to make a tomosynthetic slice.

To obtain a complete set of images for the outer areas of interest (A, B, C, D, F, G, H, and I), the areas outside the active area of the printed circuit board, shown in FIG. 5, must be positioned in the center of the inspection plane and the corresponding images taken. In reality, most areas of interest would lie inside the edge of a printed circuit board, rather than on the edge. However, since several views are acquired simultaneously at each location with the present invention, rather than sequentially, the throughput is significantly improved in comparison to known techniques.

If in the inspection plane the objects to be inspected are a grid or other arrangement (for example, joints from a Ball Grid Array), then, when the X-ray source is radiating above region of interest B, the multiple regions adjacent to B may simultaneously be radiated. Therefore, this technique may be used to acquire 8 off-axis images of 8 adjacent regions simultaneously, thus reducing the total number of imaging positions required to inspect the entire grid. In comparison, the conventional method for acquiring an image was to make 8 off-axis images sequentially for each region. Therefore, for an arrangement of N×N regions, a total number of source positions using the conventional method would be 8 times $N^2$. However, under the off-axis method of this embodiment of the invention, only one position for each region, plus a border of regions, will result in a total number of source positions equal to $(N+2)(N+2)=(N+2)^2$. As the number of regions increases, the number of source positions relative to the regions decreases dramatically in comparison to the conventional method. For example, if N=3, 72 source positions are used for the conventional method, whereas only 25 are used with the off-axis method of this embodiment. For N=10, 800 source positions are used for the conventional method, whereas only 144 positions are used for the off-axis method of this embodiment.

Once all the off-axis images have been acquired, the images may be grouped back together by grouping the images for each of the objects, i.e., images 1–8 for object A. Since all 8 images for a specific object are not acquired with the inspection plane in the same mechanical position, an image alignment technique is preferably used to merge the images together. If one uses a very accurate X-Y table that positions the images within an accuracy of 1 pixel, then the images can be simply grouped together. If the X-Y table has an accuracy of less than 1 pixel, one may need to align the various images through the use of "in-view" fiducials or alternately have sufficient overlap between the images to match them at adjacent boundaries.

Figure 6:
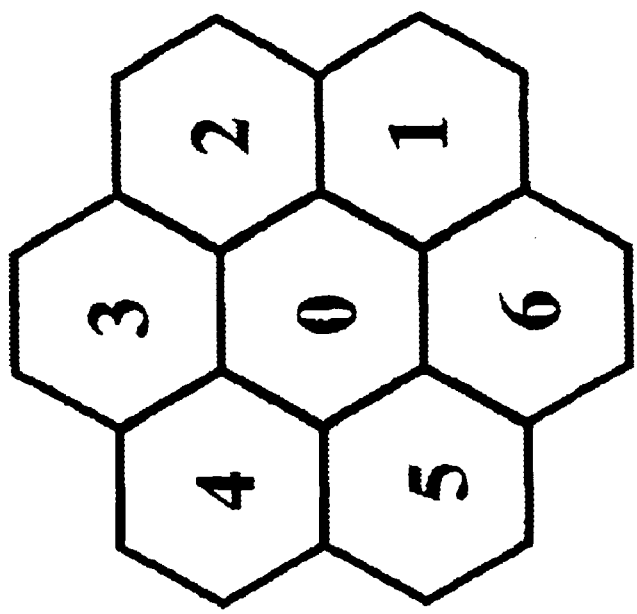
FIG. 6 is a hexagonal scan pattern in accordance with an embodiment of the present invention.

Since the corners of a square arrangement of points are farther from the center of the source to the target than the sides of the grid or square, it is more advantageous to use a pattern that keeps the center of each off-axis image a fixed radius from the center of the imaging system. FIG. 6 depicts an example of a hexagonal arrangement that accomplishes this requirement. Instead of 8 off-axis images, 6 off-axis images can be used to generate a tomosynthetic slice, and the hexagonal pattern can be symmetrically positioned at any field-of-view on the circuit board.

The detector 130 is positioned to receive the emitted X-rays and convert the X-rays to visible light. The digital output of the detector is provided to a processor 150 or an image processing system, as described above. This feature permits optimizing the field-of-view, resolution, and throughput for virtually any board type, even if the board has a wide variation of component pitch present. This unique application of the imaging system (i.e., looking at all 8 images simultaneously) eliminates the need for a detector that must be re-positioned, thereby reducing the mechanical complexity of the system (i.e., eliminates the galvonometer mirror system), improving system reliability and the repeatability of results, and reducing overall system cost. This approach simplifies the mechanical requirements for the image collection system and allows static rather than dynamic image train alignment/calibration.

In alternative embodiments, the detector 130 may be a CsI crystal detector that is viewed by a CCD camera, through, for example, a lens or a fiber-optic bundle. The analog (or digital) output of the camera is provided to a processor or an image processing system, which processes the image information to formulate an image on a display, such as a video monitor. Thus, the cost of an expensive steerable X-ray source is avoided and the overall system cost is lower.

A further embodiment of the present invention could employ a flat panel detector consisting of an amorphous selenium semiconductor X-ray absorber coating over a thin-film transistor array as the basis for digital capture. One such detector is available from Direct Radiography Corp., Newark, Del. With this detector, the X-rays are converted by the amorphous selenium directly into an electric charge that is collected by an array of electrodes. The result is a digital image that can be immediately viewed on a video monitor or passed to an image processor. Because the X-rays are converted directly into an electric charge, light scatter is avoided and the degradation of the image sharpness is eliminated.

Figure 3:
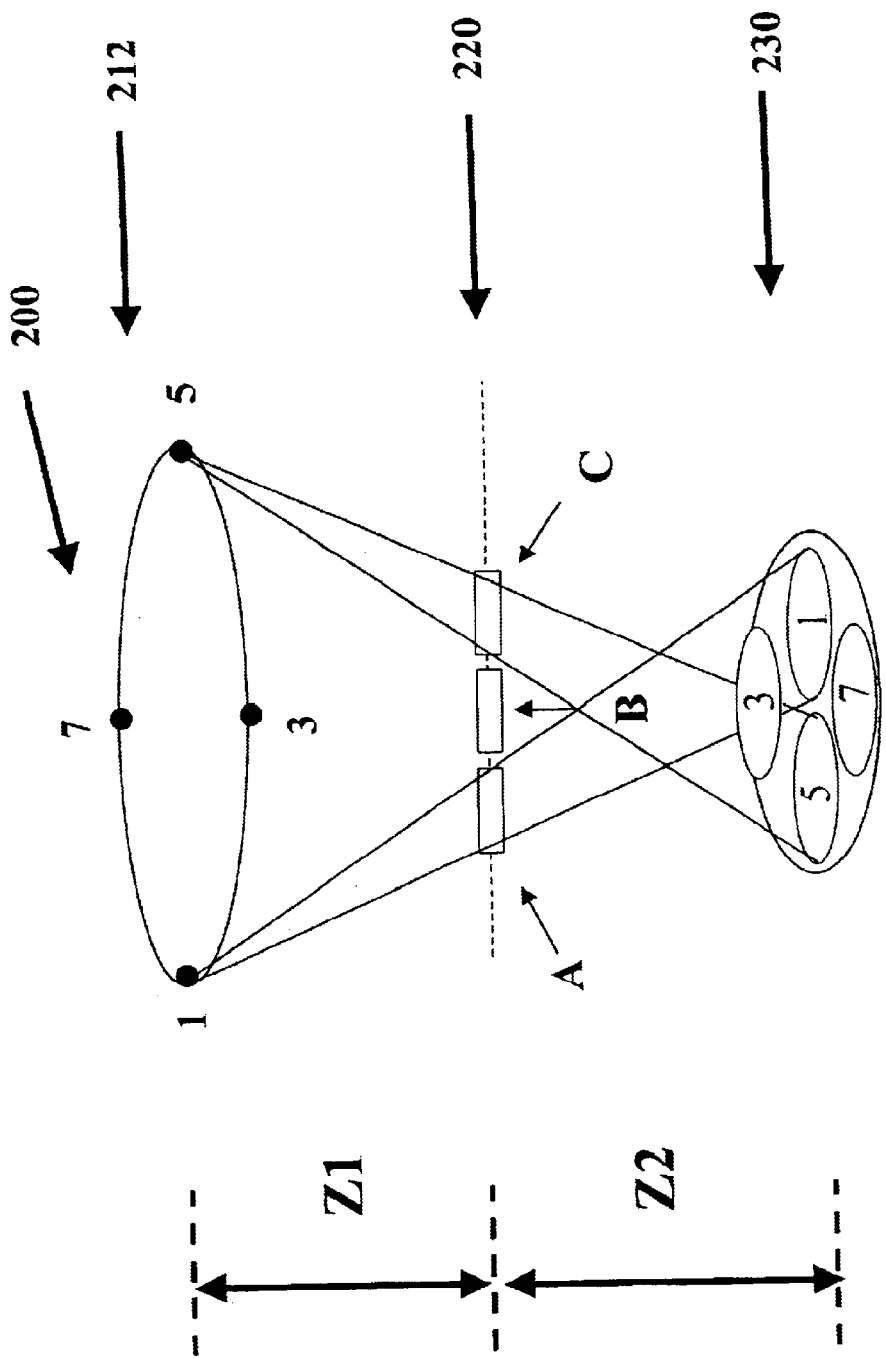
FIG. 3 is a diagrammatic illustration of another embodiment of an X-ray inspection system of the present invention.

FIG. 3 depicts another X-ray inspection system 200 embodying the principles of an alternative embodiment of the present invention. System 200 includes a steerable X-ray source 212 and a detector 230. A suitable steerable X-ray source is Model MXT-160CR, available from Nicolet Imaging Systems, San Diego, Calif. This model has a 10 micron spot size and a 75 mm steering diameter. As with the system of FIG. 1, the objects A, B, and C to be imaged may be placed on a support, such as an X-Y table (not shown), which lies in the inspection plane 220.

The detector 230 used in system 200 is preferably a high resolution, X-ray sensitive, flat screen detector. An example of such a detector is a Cesium Iodide ("CsI") crystal detector. A CsI detector comprises a flat screen made of CsI. A suitable CsI crystal detector may be obtained from Hilger Crystals, Margate, Kent, United Kingdom. The total size of a CsI crystal detector can range from 25 mm×25 mm to 75 mm×75 mm. With these CsI crystal detectors, a resolution of 30 to 40 linepairs/mm within the crystal can be obtained.

The X-ray source 212 and the detector 230 may be mounted on independent vertical drive mechanisms that allow a continuously variable field-of-view. The vertical drive mechanisms are used to vary the distance, Z1, between the X-ray source 212 and the object to be imaged, and the distance, Z2, between the object to be imaged and the detector 230. In system 200, the distance Z1 can range from approximately 0.5" to 3.0" and the distance Z2 can range from approximately 0.5" to 3.0". As a further alternative, the system may not include vertical drive mechanisms, the source 212 and the detector 230 may be positioned at fixed Z1 and Z2 distances.

Additionally, system 200 is provided with a control system, similar to that used in system 100. In addition to the functions described above with respect to system 100, the control system of system 200 steers the electron beam to the desired region of interest.

By steering the X-ray beam off the center axis, an off-axis image can be projected onto detector 230. In system 200, the images are acquired sequentially. For example, the source 212 projects X-rays from location 1 toward object A to generate an off-axis image of object A at position 1 on the detector 230 and then the source 212 may be moved to location 5 to obtain an off-axis image of object C at position 5 on the detector 230. The X-ray source 212 is repositioned and additional images of the objects are obtained. This will be better understood with the following discussion. For simplicity's sake, the discussion refers only to four images, although more images may be required for tomosynthetic reconstruction.

When area of interest A, shown in FIG. 5, is placed in the center of the inspection plane and X-rays are projected from source 212, an image of area B corresponding to position 5 will be obtained and then an image of area D corresponding to position 3. When area of interest B is placed in the center of the inspection plane, an image of area A corresponding to position 1 will be obtained, then an image of area C corresponding to position 5, and finally an image of area E corresponding to position 3. The remaining areas of interest are placed in position and the corresponding images are obtained.

The output of the detector 230 is then supplied to a camera, such as a CCD camera. The analog (or digital) output of the camera is provided to a processor or an image processing system, which processes the image formation to formulate an image that can be viewed on a display or a video monitor.

Because the images in system 200 are acquired sequentially, rather than simultaneously, as in system 100, the throughput advantage realized is not as great. However, with system 200, a larger off-axis angle (i.e., 30–35 degrees, as compared to 25–30 degrees) can be achieved before having to resort to a large format detector. Since the use of a large format detector is avoided, the overall system cost is lower. Additionally, in system 200, all of the pixels on the detector 230 are used to make each image, thereby resulting in a higher resolution (i.e., more pixels per unit area). As PCB components and their pitch become smaller, this approach likely will be required because of the better resolution that the CsI detector provides.

For image stitching the images obtained with the acquisition methods of system 100 and system 200, the fact that the support, for example an x-y table, may be less precise than the size of one pixel must be taken into consideration. For example, if the support is accurate to 3 pixels, then, without "in-view" fiducials, images could not be registered to any better accuracy than +/−3 pixels. Thus, these images, when combined for tomosynthetic reconstruction, would result in a blurred tomosynthetic slice. Consequently, each area of interest preferably has one or more "in-view" fiducials that can be used to align each image properly. For example, shape recognition algorithms could be employed to uniquely identify the same object in each of the 4 off-axis images. This object could then be used to align the images and thus remove the mechanical inaccuracy of the support. This alignment preferably includes an x-y alignment and a rotational alignment to perfectly realign the images. Therefore, depending on the shape of the fiducials, one, two or three in-view fiducials may be required.

In an alternate embodiment, linear optical encoders could be placed on an x-y table in order to improve the accuracy of the table to smaller than 1 pixel. However, this alternative would increase the overall system cost.

One example of an object that is likely to be in every area of interest is a circular hole called a "via." CAD data for the printed circuit board may be used to initially find the vias in each image. The location of each via is then compared to other nearby objects such as solder joints and integrated circuits. Each via is ranked by its distance from other possible obscuring objects. For example, the vias that are greatest distance from other objects would be assigned the highest rank. Next, X-ray images are obtained. Then the shape recognition algorithm is run to determine whether the vias could be reliably located. The vias that can be located with the highest probability are used in the final inspection list for that printed circuit board.

An example of a suitable shape recognition algorithm would be an autocorrelation technique using a template for each generic shape (i.e., circle, square, triangle, diamond, cross) of a via or other "in-view" fiducial. This template is compared with the actual region of interest in the X-ray image containing the "in-view" fiducial. A correlation matrix containing the goodness of fit of the template to each location in the region is generated. The point of highest correlation is where the template best matches the fiducial. This "in-view" fiducial is then found in the other off-axis images, which is subsequently used to align the off-axis images to a common point and thus remove any slight positioning errors caused by the x-y table.

Alternately, if a reliable "in-view" fiducial can not be located within an area of interest, then the overlap between adjacent images may be relied on in order to align the images together. For example, the adjacent edges of the image of area A corresponding to detector position 5 and the image of area B corresponding to detector position 5 may use a shape recognition algorithm to align the images together.

In accordance with a preferred embodiment, the overall scan sequence for a test object is optimized to minimize scan time. The challenges regarding scan optimization are related to two facts, (1) normally, 8 off-axis images are required to make a "good" tomosynthetic slice (instead of the 4 images described above), and (2) the fields of view may not be arrangeable on a perfectly uniform pattern. Therefore, to minimize the total number of fields of view for a PCB and to minimize the number of fields of view on the outer edges, it is desirable to perform a multi-variable optimization of the scan pattern.

While the invention has been described in connection with certain embodiments, it should be understood that it is not intended to limit the invention to these particular embodiments. To the contrary, it is intended to cover all alternatives, modifications and equivalents falling with-in the spirit and scope of the invention.

We claim:

1. An apparatus for acquiring off-axis X-ray images of a plurality of regions of interest, comprising:

a source of radiation, the source producing a beam of radiation;

a surface to support at least a subset of the plurality of regions of interest; and a X-ray detector located to simultaneously receive portions of the beam that have passed through the subset of the plurality of regions of interest, the X-ray detector producing from the received portions of the beam a plurality of discrete images, each of the plurality of discrete images being associated with a region of interest in the subset of the plurality of regions of interest;

wherein at least one of the source, the surface, and the detector may be moveable to position the regions of interest within the beam.

2. The apparatus of claim 1 wherein the electronic representations of a region of interest are transferred from the detector to a processor for processing into images of the region of interest.

3. The apparatus of claim 2 wherein the resulting images can be viewed on a display.

4. The apparatus of claim 1 further comprising a processor to combine at least two digital representations of a region of interest to produce a tomosynthetic image.

5. The apparatus of claim 1 wherein the detector comprises an amorphous silicon screen.

6. The apparatus of claim 5 wherein the detector further comprises a coating of cesium iodide.

7. The apparatus of claim 1 wherein the detector comprises a cesium iodide screen.

8. The apparatus of claim 7 wherein the detector further includes a lens or fiber optic bundle for providing a light image to a CCD camera.

9. The apparatus of claim 8 wherein the output of the CCD camera is provided to a processor for processing into images of the region of interest.

10. The apparatus of claim 1 wherein the source of radiation is a non-steerable x-ray source.

11. The apparatus of claim 1 wherein the support surface may be moveable to position the regions of interest within the beam.

12. The apparatus of claim 1 wherein the source and the detector may be moveable to position the regions within the beam.

13. A method for acquiring off-axis X-ray image data for a plurality of regions of interest, comprising the steps of
locating the plurality of regions of interest within a beam of radiation, at least a portion of the beam passing through the regions of interest;
simultaneously detecting the portion of the beam for the plurality of regions of interest and producing a plurality of discrete image data, each of said plurality of discrete image data corresponding to each of the regions of interest;
adjusting the location of the plurality of regions of interest, at least a subset of the plurality of regions of interest remaining within the beam;
repeating the step of simultaneously detecting and producing image data; and
combining image data for at least one region of interest to generate a tomosynthetic image of the region of interest.

14. The method of claim 13 wherein the combining step comprises aligning the image data for each region by locating one or more in-view fiducials in each region of interest.

15. The method of claim 13 wherein the combining step comprises aligning the image data for each region by monitoring an encoder output associated with a support for adjusting the location of the plurality of regions of interest.

16. An apparatus for acquiring off-axis X-ray images of a plurality of regions of interest, comprising:
a non-rotatable source of radiation that produces a beam;
a surface to support at least a subset of the plurality of regions of interest; and
a detector located to receive portions of the beam that pass through the subset and to simultaneously produce an electronic representation of an image for each region of interest in the subset;
wherein at least one of the source, the surface, and the detector may be moveable to position the regions of interest within the beam.

17. The apparatus of claim 16 wherein the support comprises an x-y table.

18. The apparatus of claim 17 wherein the support further comprises an encoder coupled to the x-y table, the encoder providing the x-y table with a positional accuracy required to correctly combine separate images.

19. The apparatus of claim 18 wherein the positional accuracy of the table is better than about +/−2 pixels.

20. The apparatus of claim 16 wherein at least one of the source and the detector is movable along the z-axis.

21. The apparatus of claim 16 wherein the detector converts the received portion of the beam into an image signal.

22. The apparatus of claim 21 wherein the image signal is transferred from the detector to an image processing system for processing into images of the region of interest.

23. The apparatus of claim 22 further comprising a processor for controlling the positioning of the plurality of regions of interest within the beam and the processing of the digital image signals into images of the regions of interest.

24. The apparatus of claim 22 wherein the resulting images can be viewed on a display.

25. The apparatus of claim 16 wherein the support surface may be moveable to position the regions of interest within the beam.

26. An apparatus for acquiring off-axis X-ray images of test objects comprising:
an X-ray source for producing a steerable electron beam from a number of different positions along a horizontal path perpendicular to a vertical axis, each position being at an angle from the vertical axis; and
a high-resolution detector positioned to receive X-rays that are transmitted through at least two regions of interest of the test object from each of the positions and to produce electronic representations of acquired off-axis images corresponding to the regions of interest.

27. The apparatus of claim 26 wherein the control system directs a second electron beam to a second region of interest on the test object at each position.

28. The apparatus of claim 26 wherein the image of the first region of interest corresponding to one position and the image of the second region of interest corresponding to another position are acquired sequentially.

29. The apparatus of claim 26 wherein the detector includes a screen made of cesium iodide.

30. The apparatus of claim 26 wherein the detector further includes a camera.

31. A method for simultaneously acquiring a plurality of off-axis X-ray images comprising:
placing a test object with at least two regions of interest on an inspection plane;
directing X-ray beams to the regions of interest, the X-ray beams being directed off-axis with respect to a vertical axis through the inspection plane;
receiving on a detector X-rays that are transmitted through the regions of interest; and
simultaneously producing electronic representations of acquired off-axis images corresponding to the regions of interest.

32. The method of claim 31 wherein the directing step comprises generating X-ray beams from a non-steerable source of radiation.

33. The method of claim 31 wherein the producing step further comprises aligning the acquired off-axis images for each region of interest by locating one or more in-view fiducials in each image of the respective region.

34. A method for acquiring a plurality of off-axis X-ray images comprising:
placing a test object with at least two regions of interest on an inspection plane;
producing a steerable X-ray beam from a number of different positions along a horizontal path perpendicular to a vertical axis;
directing an X-ray beam to a first region of interest;
receiving on a detector X-rays that are transmitted through the first region of interest;
directing an X-ray beam to a second region of interest;
receiving on the detector X-rays that are transmitted through the second region of interest; and
producing electronic representations of acquired off-axis images corresponding to the regions of interest.

* * * * *